United States Patent
Colm et al.

(10) Patent No.: US 9,651,161 B2
(45) Date of Patent: May 16, 2017

(54) CHECK VALVE, ESPECIALLY FOR MEDICAL APPLICATIONS

(75) Inventors: Michael Carmody Colm, Listowel (IE); Brendan Casey, Thurles (IE); Gerard Gabriel Henn, Limerick (IE)

(73) Assignee: ILLINOIS TOOL WORKS INC., Glenview, IL (US)

( * ) Notice: Subject to any disclaimer, the term of this patent is extended or adjusted under 35 U.S.C. 154(b) by 992 days.

(21) Appl. No.: 14/354,181

(22) PCT Filed: Feb. 24, 2011

(86) PCT No.: PCT/EP2011/052763
§ 371 (c)(1),
(2), (4) Date: Apr. 25, 2014

(87) PCT Pub. No.: WO2011/151090
PCT Pub. Date: Dec. 8, 2011

(65) Prior Publication Data
US 2014/0299212 A1  Oct. 9, 2014

(30) Foreign Application Priority Data
Jun. 1, 2010  (DE) .................. 10 2010 022 410

(51) Int. Cl.
*F16K 15/14* (2006.01)
*A61M 39/24* (2006.01)

(52) U.S. Cl.
CPC .......... *F16K 15/144* (2013.01); *A61M 39/24* (2013.01); *A61M 2039/246* (2013.01); *Y10T 137/7879* (2015.04)

(58) Field of Classification Search
CPC .... F16K 15/144; F16K 15/145; F16K 15/147; Y10T 137/7879; A61M 39/24;
(Continued)

(56) References Cited

U.S. PATENT DOCUMENTS 5,727,594 A  3/1998 Choksi
5,992,462 A * 11/1999 Atkinson .............. A61M 39/24
137/515.5

(Continued)

FOREIGN PATENT DOCUMENTS

DE  4309262 A1  6/1994
DE  202004009521 U1  9/2004
(Continued)

OTHER PUBLICATIONS

ISR for PCT/EP2011/052763 mailed May 20, 2011.
DE Search Report for 10 2010 022 410.3 mailed Mar. 15, 2011.

*Primary Examiner* — Richard K Durden
(74) *Attorney, Agent, or Firm* — Hauptman Ham, LLP

(57) ABSTRACT

A non-return valve, in particular for medical purposes, including a first hose connection housing, a second hose connection housing and a membrane disk which is made from flexible material. The membrane disk is arranged between the two hose connection housings and can be raised up from an annular valve seat in communication with an inlet space which is connected to an inlet passage. A medium-permeable formation which faces the membrane disk is arranged on the inlet side into the inlet space, supporting the membrane disk against overextension in the case of high return pressures.

14 Claims, 9 Drawing Sheets

(58) Field of Classification Search
CPC .... A61M 2039/246; A61M 2039/2433; A61M 2039/2446
USPC ............... 137/859, 515, 516.11, 516.13
See application file for complete search history.

(56) References Cited

U.S. PATENT DOCUMENTS

| | | | |
|---|---|---|---|
| 6,390,120 B1 | 5/2002 | Guala | |
| 7,673,653 B2 * | 3/2010 | Mijers | ................... F16K 15/144 137/843 |
| 8,251,099 B2 | 8/2012 | Carmody et al. | |
| 2004/0188541 A1 | 9/2004 | Maruyama | |
| 2007/0167058 A1 * | 7/2007 | Mijers | ................... A61M 39/24 439/288 |

FOREIGN PATENT DOCUMENTS

| | | |
|---|---|---|
| DE | 202006016730 U1 | 1/2007 |
| DE | 202008001077 U1 | 5/2008 |
| EP | 1099457 A2 | 5/2001 |
| GB | 690897 A | 4/1953 |
| WO | 96/24791 A1 | 8/1996 |
| WO | 2005123176 A1 | 12/2005 |

* cited by examiner

Fig. 9
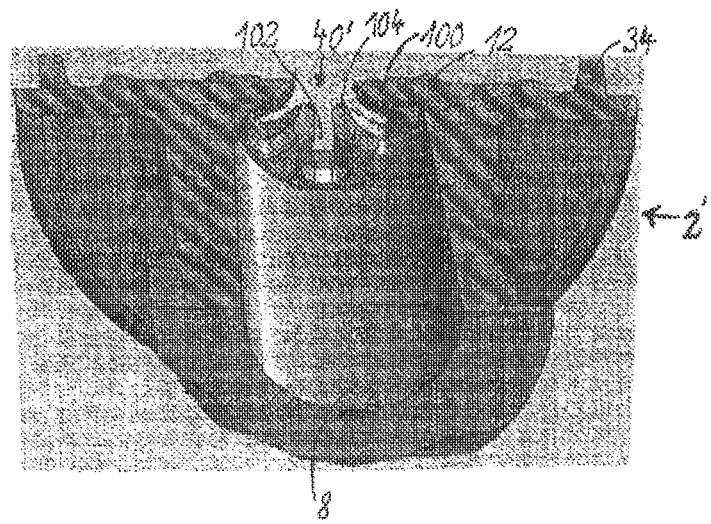
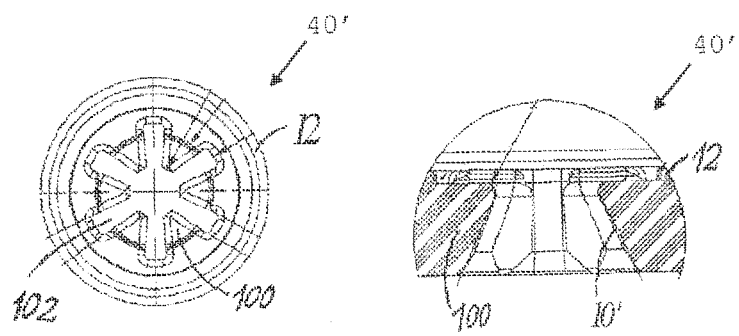
Fig. 10  Fig. 11

CHECK VALVE, ESPECIALLY FOR MEDICAL APPLICATIONS

RELATED APPLICATIONS

The present application is a National Phase of International Application Number PCT/EP2011/052763 filed Feb. 24, 2011 and claims priority to German Application Number 10 2010 022 410.3 filed Jun. 1, 2010.

TECHNICAL FIELD

The invention relates to a non-return valve, in particular for medical applications, having a first hose connection housing and a second hose connection housing and a membrane disk which is made from flexible material. The membrane disk is arranged between the two hose connection housings, can be raised up, in the case of positive pressure in an inlet passage in the first hose connection housing, from an annular valve seat which surrounds an inlet space which is connected to the inlet passage, and, in the case of positive pressure in an outlet passage, can be pressed on the valve seat reliably and in minimum times, the membrane disk being provided on its outermost circumferential region with an annular bead which is received in annular grooves, lying opposite one another, of the hose connection housings, the membrane disk being provided radially outside the valve seat with openings which are connected to an outlet space.

PRIOR ART

A non-return valve of this design is known according to an earlier proposal of the applicant from German utility model 20 2006 016 730.7. This known valve is designed, in particular, for relatively high pressures.

Furthermore, a further non-return valve having the above-mentioned features is also likewise known according to an earlier proposal of the applicant from German utility model 20 2004 009 521.1, which non-return valve is designed, in particular, for relatively low pressures.

Certain practical problems have resulted during the practical use of said known valves which differ substantially as a result of the design of the second hose connection housing in accordance with the pressure ranges, in which they are to be used. Non-return valves of this type are used in hospitals, in particular in infusion sets, it being possible for said non-return valves to be exposed sometimes to very high pressures in the return flow direction, depending on the specific configuration of the infusion set, which very high pressures can reach values of up to 325 psi (22.4 bar). In the case of high pressures of this type in the return flow direction, the membrane disk which is made from the flexible material which is usually silicone is deflected to a pronounced extent within the non-return valve counter to the inflow direction.

In the case of the two known non-return valves of the type specified above, the inlet is configured in the first hose connection housing as a simple open bore which is surrounded by the valve seat. If the above-mentioned high pressures in the reverse direction then occur here, the membrane disk can be deflected in a rearward and downward manner into the open bore and can be extended here beyond its elastic limits. This can in turn lead to the loss of the non-return valve function.

Proceeding from a non-return valve of the type which is specified above, the invention is therefore based on the object of improving the known valve in such a way that it becomes insensitive with respect to high pressures counter to the inflow direction and, in particular, damage to the membrane disk can no longer occur.

SUMMARY OF THE INVENTION

According to the invention, this object is achieved by virtue of the fact that a medium-permeable formation which faces the membrane disk is arranged on the inlet side in the inlet space, which formation supports the membrane disk against overextension in the case of high return pressures. It is clear that the above-mentioned problems are avoided completely as a result of this.

In one preferred embodiment according to the invention, said formation is of cross-shaped configuration in the inlet space of the valve.

In detail, the invention can be developed by virtue of the fact that circular segment-shaped inlet openings are formed between the struts which form the cross-shaped formation.

In one preferred embodiment according to the invention, that side of the cross-shaped formation which faces the membrane disk is configured as a planar supporting face.

In detail, it is particularly advantageous that the underside, facing counter to the inflow direction, of the formation is of hydrodynamic configuration. As a result, flow losses and possible eddying of the medical liquids which flow through here are avoided.

For this purpose, oblique faces which taper toward one another are preferably provided on the underside of the formation.

It is provided in one particularly preferred embodiment according to the invention that the outer ends of the struts which form the cross-shaped formation merge into an annular supporting face, the planar upper side of which supplements the supporting face, facing the membrane disk, of the formation. As a result, additional security against extension of the membrane is achieved.

In detail, it is particularly advantageous that the upper edge of the formation and the annular supporting face is configured to be rounded or with a bevel. As a result, particularly gentle support of the membrane disk is achieved, with the result that the latter, even if it is pressed into the inlet openings under high pressure, cannot be damaged in any way.

In order to reduce the flow resistance of the non-return valve according to the invention in the passage direction further, it is particularly preferred if the formation comprises arms which protrude radially into the inlet space.

It is particularly preferred for this purpose if the arms do not meet in the center of the inlet space, with the result that a passage of small diameter remains open there.

In order nevertheless to achieve a sufficient supporting force, it is preferred if the arms are designed so as to taper in a V-shaped manner toward the center of the inlet space.

It is particularly preferred here if the arms are configured in such a way that they form virtually rectangular slots with parallel side edges between them.

A particularly satisfactory distribution of force results if six arms which are spaced apart identically are provided.

A further reduction in the throughflow resistance results if the arms are beveled on their front edges, with the result that the spacing between the arms is reduced in the throughflow direction.

Furthermore, it is particularly preferred that the formation is configured in one piece with the first hose connection housing.

BRIEF DESCRIPTION OF THE DRAWINGS

In the following text, the invention will be explained in greater detail using embodiments which are illustrated by way of example in the drawings, in which:

FIG. 9 shows a perspective, partially sectioned view of FIG. 8, obliquely from below, FIG. 10 shows the detail of the medium-permeable formation according to the further embodiment of the present invention, and FIG. 11 shows a side sectional illustration of the detail from FIG. 10.

DETAILED DESCRIPTION

Figure 1:
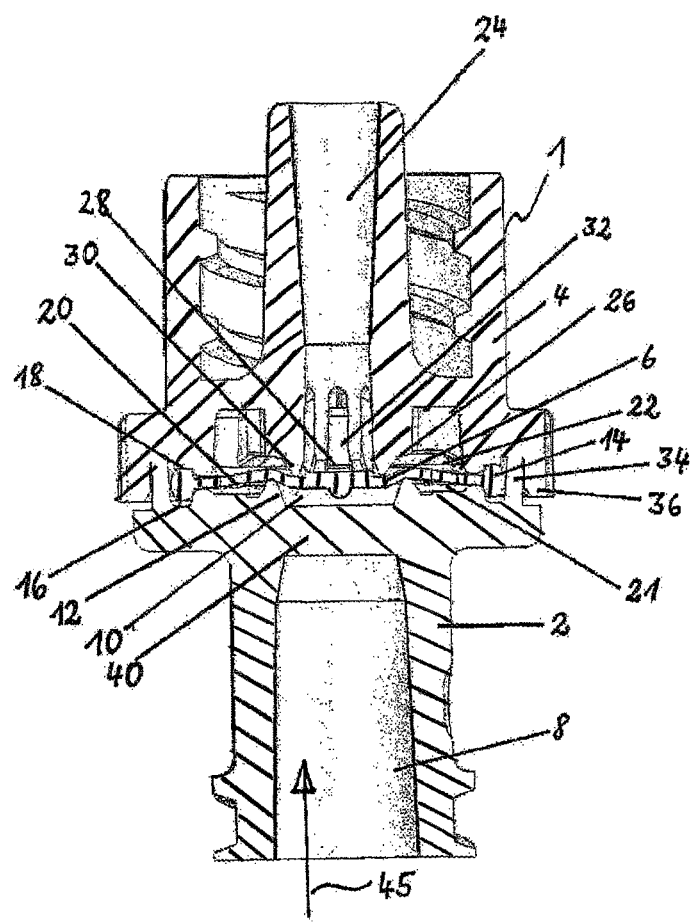
FIG. 1 shows a side sectional view of the non-return valve according to the invention in the rest state.
Figure 2:
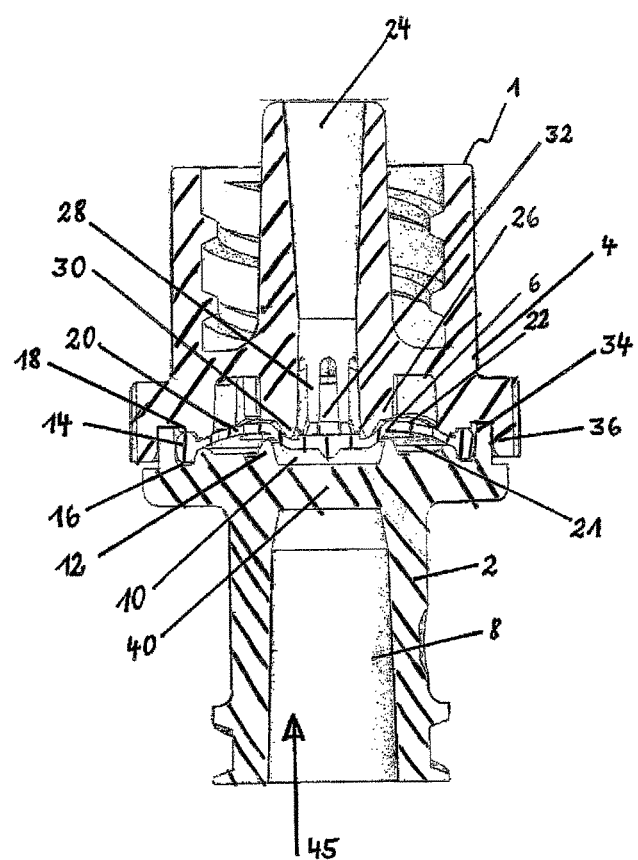
FIG. 2 shows a view, corresponding to FIG. 1, of the non-return valve during the inflow of a liquid.
Figure 3:
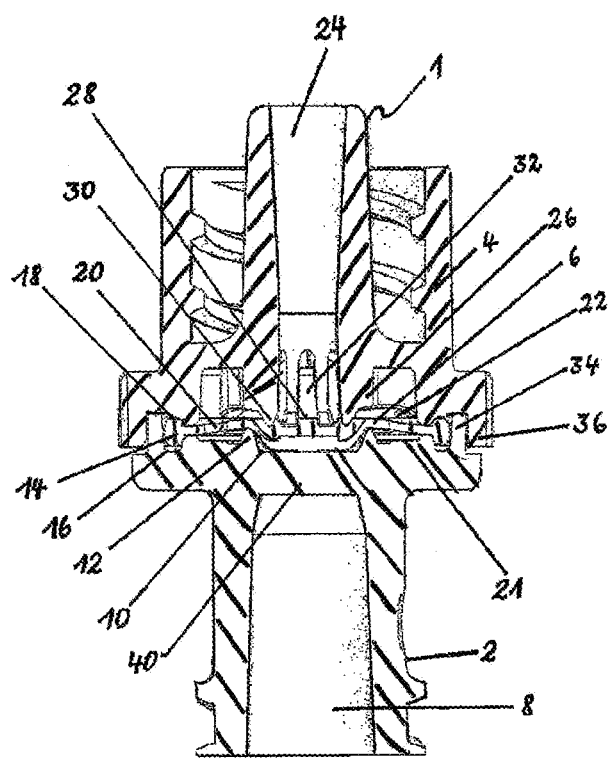
FIG. 3 shows a view, corresponding to FIGS. 1 and 2, of the non-return valve in the case of the occurrence of an increased pressure counter to the inflow direction.

The non-return valve 1 which is shown in FIGS. 1 to 3 is suitable, in particular, for medical purposes and covers, for example, pressure differences from high pressures down to 0.002 bar. The non-return valve 1 consists of a first hose connection housing 2 and a second hose connection housing 4 which are produced, for example, from plastic by way of injection molding, and a membrane disk 6 which is arranged between the two hose connection housings 2 and 4 and is composed of a flexible plastic, for example silicone.

The first hose connection housing 2 has an inlet passage 8 which opens into an inlet space 10. The inlet space 10 is surrounded by an annular valve seat 12 which is prestressed against the membrane disk 6.

The membrane disk 6 is of continuous configuration without openings in its region which lies inside the valve seat 12, with the result that considerable tensile forces can be transmitted radially from the inside to the outside and vice versa. On its outermost circumferential region, the membrane disk 6 is provided with an annular bead 14 which is molded, for example, onto the membrane disk 6 if the latter has likewise been produced by injection molding of the silicone. In the first hose connection housing 2, an annular groove 16 is formed close to its outer edge in the end face of the hose connection housing 2, opposite which annular groove 16 an annular groove 18 of the second hose connection housing 4 lies in the assembled state. If the first hose connection housing 2 is connected to the second hose connection housing 4 during the assembly of the non-return valve 1, for example by adhesive bonding or ultrasonic welding, the annular bead 14 is received in the annular grooves 16 and 18, which lie opposite one another, of the two hose connection housings 2 and 4, and the membrane disk 6 is at the same time prestressed against the valve seat 12.

Furthermore, as shown in FIGS. 1 to 3, the membrane disk 6 is provided radially outside the valve seat 12 with openings 20 which are arranged on a radius and connect an annular space 21 which lies radially outside the valve seat 12 in the first hose connection housing 2 to an outlet space 22 of the second hose connection housing 4, which outlet space 22 for its part is connected to the outlet passage 24 of the second hose connection housing 4.

The outlet space 22 is delimited at the top by the wall 26 of the second hose connection housing 4 which lies opposite the membrane disk 6. Protruding medium-permeable formations which are denoted in general by 28 are provided on the wall 26, which formations support the membrane disk 6 against the opening pressure and at the same time prestress the membrane disk 6 in the direction of the inlet space 10, the formation 28 lying inside the boundary which is produced by the valve seat 12.

The formation 28 consists of a number of projections 30 which surround the inlet opening 32, emanating from the outlet space 22, of the outlet passage 24 in a crown-shaped manner.

For assembly, the two hose connection housings 2 and 4 can be connected so as to engage into one another by means of an inner annular projection 34 on the first hose connection housing 2 and an outer annular projection 36 on the second hose connection housing 4. After this connection has been produced, the final assembly can take place, for example, by way of ultrasonic welding. FIGS. 1 to 3 show a medium-permeable formation 40 which faces the membrane disk 6 on the inlet side into the inlet space 10, which formation 40 supports the membrane disk 6 against overextension in the case of high return pressures. Said medium-permeable formation 40 will be explained in greater detail further below with reference to FIGS. 4 to 7.

In the illustration in FIG. 1, the non-return valve 1 is illustrated in its closed rest state. In the illustration of FIG. 2, a medical liquid, for example, flows through the non-return valve 1 in the direction of the arrow 45, with the result that the membrane disk 6 is raised up from the valve seat 12 and the liquid can flow through the openings 20 in the membrane disk 6 and the crown-shaped formation 28 to the outlet passage.

FIG. 3 shows the state if a pronounced return pressure occurs from the outlet passage 24 in the direction of the inlet passage 8 in the non-return valve 1. In this state, as shown in FIG. 3, the membrane disk 6 is deformed downward into the inlet space 10 and is supported by the formation 40 in the inlet space 10 in order to avoid overextension.

FIGS. 4 to 7, to which reference will be made in the following text, show further details of the first hose connection housing 2 with the medium-permeable formation which is contained therein and is configured in one piece.

As shown, in the preferred embodiment which is shown, the formation 40 in the opening of the inlet passage 8 into the inlet space 10 is of cross-shaped configuration. The struts 52 and 54 which form the cross-shaped formation 40 leave circular segment-shaped inlet openings 56 free, through which the medical liquid can flow from the inlet passage 8 into the inlet space 10.

Figure 4:
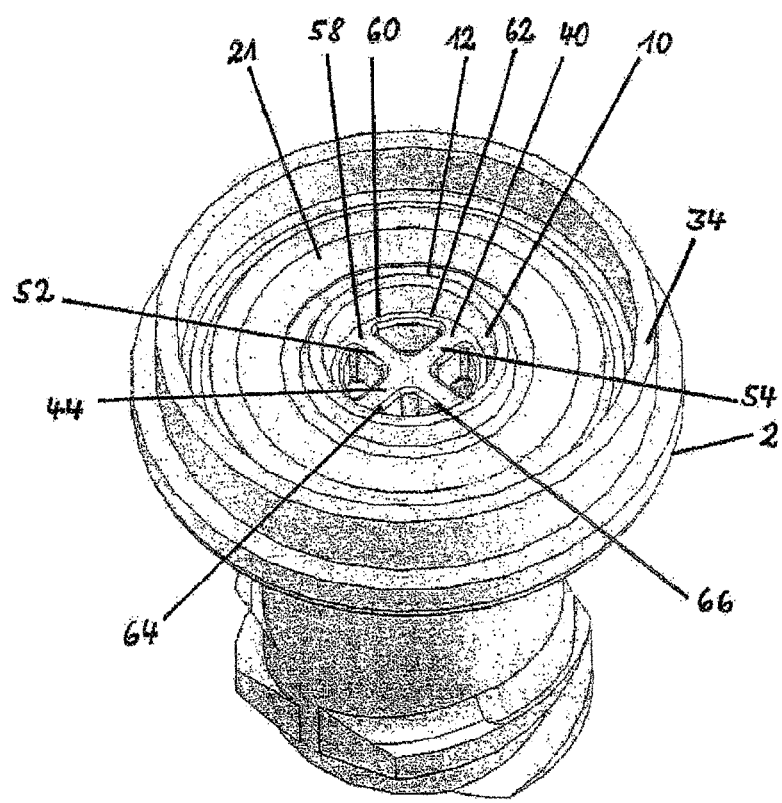
FIG. 4 shows a perspective view of the first hose connection housing on an enlarged scale, obliquely from above.

The upper side of the cross-shaped formation 40 in the illustration of FIG. 4, is configured as a planar supporting face 44 for the underside of the membrane disk 6.

Figure 6:
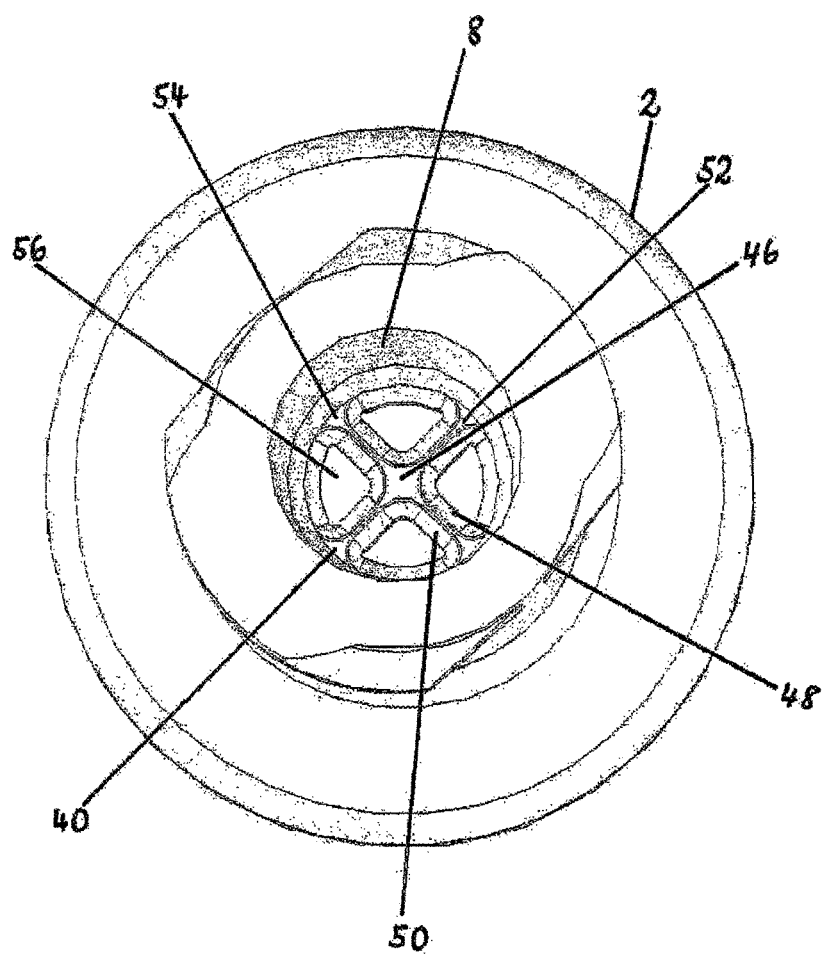
FIG. 6 shows a plan view of the first hose connection housing according to FIG. 4.
Figure 7:
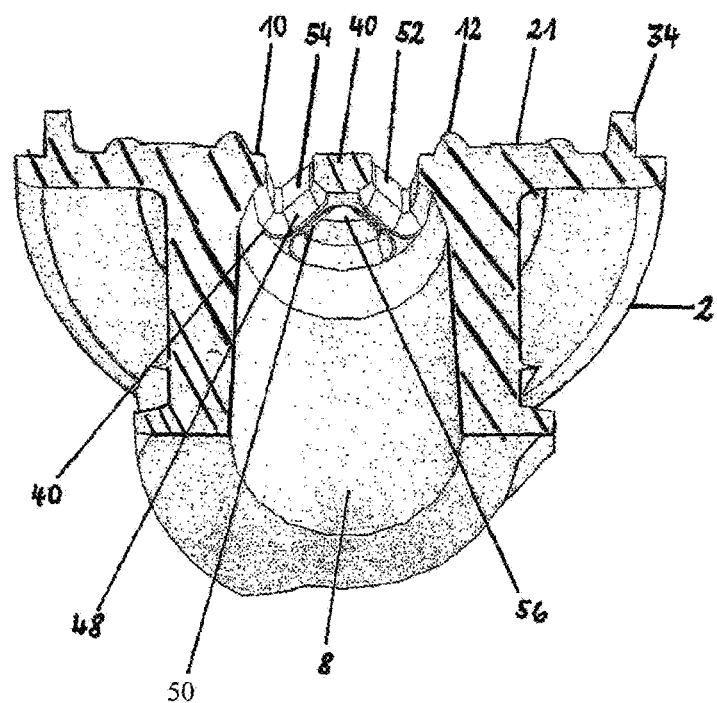
FIG. 7 shows a perspective, partially sectioned view from FIG. 4, obliquely from below.

Furthermore, as can be seen from FIGS. 6 and 7, the underside 46, facing opposite the inflow direction 45, of the formation 40, that is to say of the configuration of struts 52 and 54 is that of a hydrodynamic configuration, this being affected in the illustrated embodiment by virtue of the fact that oblique faces 48 and 50, which taper toward one another, are provided on the underside 46 of the formation 40.

Figure 5:
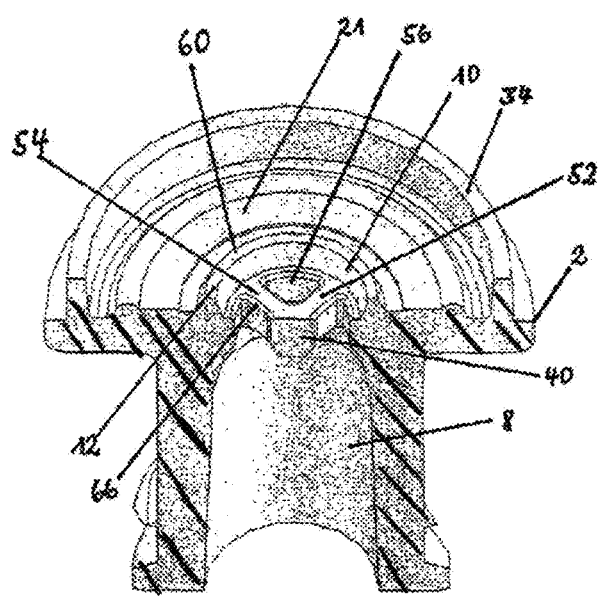
FIG. 5 shows a perspective, partially sectioned view from FIG. 4.

In order to further improve the support of the membrane disk 6 in the case of excessively high return pressures, as can be seen from FIGS. 4 and 5, the outer ends 58 of the struts 52 and 54 which form the cross-shaped formation 40 merge into an annular supporting face 60, the planar upper side 62 of which supplements the supporting face 44, which faces the membrane disk 6, of the formation 40.

Furthermore, it can be seen from FIGS. 4 and 5 that the upper edge 64 of the formation 40 and the annular supporting face 60 is preferably configured to be rounded or with a bevel 66, in order to avoid the membrane disk 6 being damaged if the return pressure is so great that regions of the membrane disk 6 are pressed into the inlet openings 56.

Figure 8:
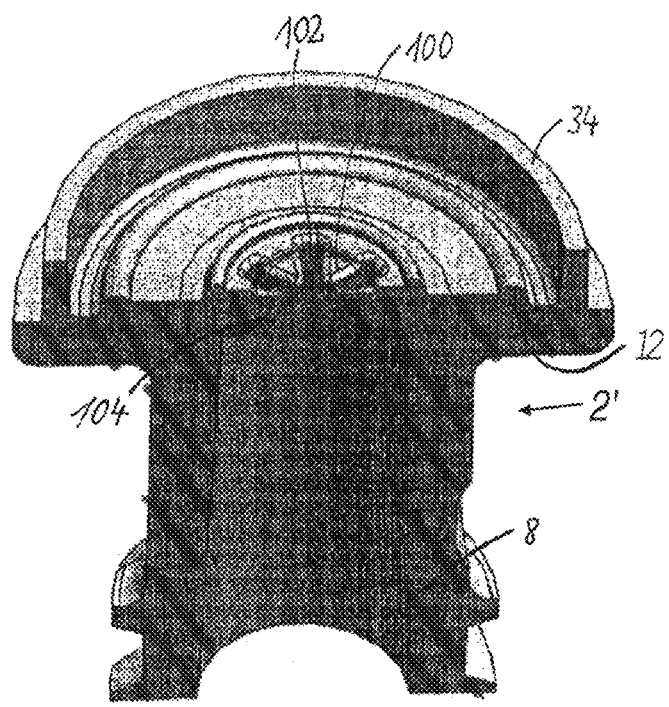
FIG. 8 shows a cross-sectional perspective view of a further embodiment of the first hose connection housing on an enlarged scale, obliquely from above.

FIGS. 8 and 9 show a further embodiment for a non-return valve 1' according to the invention. The latter has a particularly low flow resistance in the passage direction. The non-return valve 1' according to the invention consists of a first hose connection housing 2' and a second hose connection housing 4 which can be produced, for example, from plastic by way of injection molding, and a membrane disk 6 which is arranged between the two hose connection housings 2' and 4 and consists of a flexible plastic, for example silicone.

Here and in the following text, the same designations are used for identical objects, in order to improve the comprehensibility of the description and the comparability of the two embodiments of the invention. The designations for modified constituent parts of the further embodiment are provided with a prime.

It is also the case in this second embodiment that the first (lower in the drawings) hose connection housing 2' has an inlet passage 8 which opens into an inlet space 10. The inlet space 10 is surrounded by an annular valve seat 12, against which the membrane disk 6 is prestressed.

The membrane disk 6 is of continuous configuration without openings in its region which lies inside the valve seat 12, with the result that considerable tensile forces can be transmitted radially from the inside to the outside and vice versa. On its outermost circumferential region, the membrane disk 6 is provided with an annular bead 14 which is molded, for example, onto the membrane disk 6 if the latter has likewise been produced by way of injection molding of the silicone. In the first hose connection housing 2', an annular groove 16 is formed close to its outer edge in the end face of the hose connection housing 2, opposite which annular groove 16 an annular groove 18 of the second hose connection housing 4 lies in the assembled state. If the first hose connection housing 2' is connected to the second hose connection housing 4 during the assembly of the non-return valve 1', for example by way of adhesive bonding or ultrasonic welding, the annular bead 14 is received in the annular grooves 16 and 18, which lie opposite one another, of the two hose connection housings 2' and 4, and at the same time the membrane disk 6 is prestressed against the valve seat 12.

As shown in FIGS. 8 and 9, the membrane disk 6 is provided radially outside the valve seat 12 with openings 20 which are arranged on a radius and connect an annular space 21 which lies radially outside the valve seat 12 in the first hose connection housing 2' to an outlet space 22 of the second hose connection housing 4, which outlet space 22 for its part is in connection with the outlet passage 24 of the second hose connection housing 4.

The outlet space 22 is connected to the outlet passage 24 via a crown-shaped formation 28 which has a plurality of inlet openings 32 which run in the throughflow direction. This crown-shaped formation supports the membrane disk 6 if required against the opening pressure.

For assembly, the two hose connection housings 2' and 4 can be connected so as to engage into one another by means of an inner annular projection 34 on the first hose connection housing 2' and an outer annular projection 36 on the second hose connection housing 4. After this connection has been produced, the final assembly can take place, for example, by way of ultrasonic welding.

FIGS. 8 and 9 and 10 and 11, to which the description in the following text makes reference, show the first hose connection housing 2' with the medium-permeable formation 40' which is of clearly different configuration in this embodiment.

In this further embodiment of the invention, the formation 40' comprises arms 100 which are configured in one piece with the hose connection housing 2' and extend from the valve seat 12 radially to the inside. Here, said arms 100 do not extend quite as far as the center of the inlet space 10, but rather the radially inner ends of the arms 100 maintain a certain spacing from one another, with the result that a round passage with a relatively small diameter remains open between said arms 100. The arms 100 themselves have an inwardly tapering V-shaped structure which is designed in such a way that there are slots 102 between the arms, which slots 102 have a substantially rectangular shape with virtually parallel side edges. As an alternative, said side edges can also run radially. In the present embodiment, six arms 100 are provided.

The front edges of the arms 100 are beveled in such a way that the passage space between the arms narrows increasingly in the throughflow direction. From there, the bevels 104 merge in a rounded manner into the surface of the arms 100.

In this further embodiment of the invention, a substantially lower flow resistance in the throughflow direction is achieved by way of the specific design of the arms 100 and the additional beveling 104 than in the embodiment according to FIGS. 1 to 7.

The invention claimed is:

1. Non-return valve comprising a first hose connection housing and a second hose connection housing and a membrane disk which is made from flexible material,
    said membrane disk being arranged between the two hose connection housings, can be raised up, in the case of positive pressure in an inlet passage in the first hose connection housing, from an annular valve seat which surrounds an inlet space which is connected to the inlet passage,
    and, in the case of positive pressure in an outlet passage, can be pressed reliably and within minimal times on the valve seat, the membrane disk being provided on its outer circumference with an annular bead which is received in annular grooves, lying opposite one another, of the hose connection housings, the membrane disk being provided radially outside the valve seat with openings which are connected to an outlet space, wherein a medium-permeable formation which faces the membrane disk is arranged on the inlet side in the inlet space, said medium-permeable formation supports the membrane disk against overextension in the case of high return pressures, wherein the medium-permeable formation comprises arms which protrude radially into the inlet space, and at least one of:
the arms are cantilever beams;
the arms taper in a V-shaped manner toward the center of the inlet space such that the tip of the V is free of contact with another arm;
the arms are free of contact with each other; or
the arms have ends that do not meet in the center of the inlet space, with the result that a passage of relatively small diameter remains open there such that a path exists lying on a plane normal to the longitudinal axis of the annular valve seat that extends through the arms, an unobstructed passage exists from the center of the inlet space to a base of one of the arms, where the arm is directly connected to the respective housing to which the arm is attached at the base.

2. Non-return valve according to claim 1, wherein a side of the medium-permeable formation which faces the membrane disk is configured as a planar supporting face.

3. Non-return valve according to claim 1, wherein an underside, facing counter to an inflow direction, of the medium-permeable formation is of hydrodynamic configuration.

4. Non-return valve according to claim 3, wherein oblique faces which taper toward one another are provided on the underside of the medium-permeable formation.

5. The non-return valve according to claim 1, wherein the arms are configured in such a way that they form substantially rectangular slots with substantially parallel side edges between them.

6. The non-return valve according to claim 1, wherein six arms which are spaced apart identically are provided.

7. Non-return valve according to claim 1, wherein the arms are cantilever beams.

8. The non-return valve according to claim 1, wherein the arms taper in the V-shaped manner toward the center of the inlet space such that the tip of the V is free of contact with another arm.

9. The non-return valve according to claim 1, wherein the arms are free of contact with each other.

10. Non-return valve according to claim 1, wherein the arms have ends that do not meet in the center of the inlet space, with the result that the passage of relatively small diameter remains open there such that the path exists lying on the plane normal to the longitudinal axis of the annular valve seat that extends through the arms, the unobstructed passage exists from the center of the inlet space to the base of the one of the arms, where the arm is directly connected to the respective housing to which the arm is attached at the base.

11. A non-return valve for medical applications comprising a first hose connection housing and a second hose connection housing and a membrane disk which is made from a flexible material, said membrane disk being arranged between the two hose connection housings, can be raised up, in the case of positive pressure in an inlet passage in the first hose connection housing, from an annular valve seat which surrounds an inlet space which is connected to the inlet passage, and, in the case of positive pressure in an outlet passage, can be pressed on the valve seat, the membrane disk being provided on its outer circumference with an annular bead which is received in annular grooves, lying opposite one another, of the hose connection housings, the membrane disk being provided radially outside the valve seat with openings which are connected to an outlet space, wherein a medium-permeable formation which faces the membrane disk is arranged on the inlet side in the inlet space, said formation supports the membrane disk against overextension in the case of high return pressures wherein
the medium-permeable formation comprises arms which protrude radially into the inlet space,
the arms do not meet in the center of the inlet space, with the result that a passage of relatively small diameter remains open there, and
each of the arms is beveled on a front edge, with the result that the spacing between the arms is reduced in a throughflow direction.

12. The non-return valve according to claim 11, wherein the arms are designed so as to taper in a V-shaped manner toward the center of the inlet space.

13. The non-return valve according to claim 12, wherein the arms are configured in such a way that they form substantially rectangular slots with substantially-parallel side edges between them.

14. The non-return valve according to claim 11, wherein six arms which are spaced apart identically are provided.

* * * * *